United States Patent [19]

Shannon

[11] Patent Number: 5,202,053

[45] Date of Patent: Apr. 13, 1993

[54] POLYMERIZABLE NEMATIC MONOMER COMPOSITIONS

[75] Inventor: Paul J. Shannon, Exton, Pa.

[73] Assignee: Hercules Incorporated, Wilmington, Del.

[21] Appl. No.: 658,915

[22] Filed: Feb. 22, 1991

[51] Int. Cl.$^5$ .................. C09K 19/52; C09K 19/12; C08F 18/00; C08F 18/16

[52] U.S. Cl. .................. 252/299.01; 252/299.66; 252/299.67; 526/320; 526/326

[58] Field of Search .............. 252/299.01, 299.66, 252/299.67, 582; 359/102, 106; 526/320, 326

[56] References Cited

U.S. PATENT DOCUMENTS

| | | | |
|---|---|---|---|
| 4,637,896 | 1/1987 | Shannon | 252/582 |
| 4,810,433 | 3/1989 | Takayanagi et al. | 264/22 |
| 4,882,402 | 11/1989 | Leslie et al. | 252/299.01 |
| 4,894,263 | 1/1990 | DuBois et al. | 252/299.01 |
| 4,944,896 | 7/1990 | DeMartino et al. | 252/299.01 |
| 4,962,160 | 10/1990 | DeMartino | 525/404 |
| 4,983,318 | 1/1991 | Matsumoto et al. | 252/299.01 |
| 5,024,784 | 6/1991 | Eich et al. | 252/299.01 |
| 5,073,294 | 12/1991 | Shannon et al. | 252/299.01 |

FOREIGN PATENT DOCUMENTS 2722589 11/1978 Fed. Rep. of Germany .
62-70406 3/1987 Japan .

OTHER PUBLICATIONS

"Thermotropic Liquid-Crystalline Polymers-IV", Comb-Like Liquid-Crystalline Polymers of the Smectic and Nematic Type With Cyanobiphenyl Groups in the Side-Chains, Shibaev et al., Eur. Poly. J.

"Synthesis and Phase Behavior of Liquid Crystalline Polyacrylates", Portugall et al., Makromol Chem., 183,2311 (1982).

"Nonlinear Optical Phenomena in Liquid Crystalline Side Chain Polymers", Wendorf et al., Mol. Cryst. Liq. Cryst., vol. 169, pp. 133-136 (1989).

Primary Examiner—Robert L. Stoll
Assistant Examiner—Philip Tucker
Attorney, Agent, or Firm—Mark D. Kuller

[57] ABSTRACT

This invention is a polymerizable nematic monomer composition comprising (A) 20 to 80 weight % of at least one monomer having the following general formula wherein n is 10, 12 or 14, and (B) 80 to 20 weight % of at least one monomer having the following general formula wherein n is 4, 6 or 8:

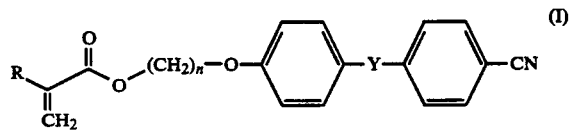

wherein R is $CH_3$ or H and Y is covalent bond or $-CO_2-$.

9 Claims, No Drawings

POLYMERIZABLE NEMATIC MONOMER COMPOSITIONS

This invention is directed to novel polymerizable nematic monomer compositions.

BACKGROUND OF THE INVENTION

Liquid crystalline monomers and mixtures of monomers in combination with photoinitiators can exhibit nematic mesophases. Under ultraviolet ("UV") irradiation these nematic mesophases can undergo rapid photopolymerization, in the presence of UV-photoinitiators, to freeze-in the structure and orientation (alignment) of the nematic mesophase into a polymer matrix.

For instance, Japanese 62 70,406 describes the polymerization of nematic monomers in the liquid crystalline state in the presence of a polymerization initiator with ultraviolet radiation. One or more of the monomers are heated to melt and then cooled into their nematic mesophase. The mesophase is aligned and photopolymerized to obtain an aligned polymer film. The monomers disclosed have the following structure:

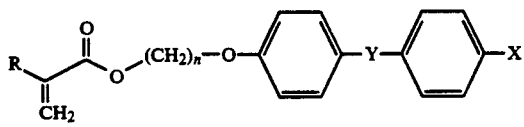

wherein n is 2, 3, 4, 5, 6, 8 or 11, X is -CN, H, Cl, etc., R is $CH_3$ or H, and Y is covalent bond or $—CO_2—$.

It has been found that compositions disclosed in the cited patent are of limited usefulness in photopolymerization processes because single monomers or mixtures of the monomers disclosed undergo rapid crystallization from the monotropic nematic phase, thus destroying the desired oriented nematic structure before photopolymerization can be performed. Therefore, it is desirable to have polymerizable nematic monomer mixtures that resist crystallization at room temperature.

SUMMARY OF THE INVENTION

This invention is a polymerizable nematic monomer composition comprising (A) 20 to 80 weight % of at least one monomer having the following general formula wherein n is 10, 12 or 14, and (B) 80 to 20 weight % of at least one monomer having the following general formula wherein n is 4, 6 or 8:

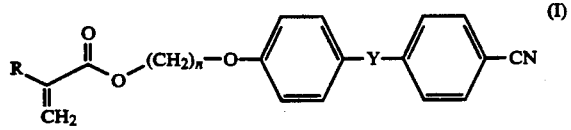

(I)

wherein R is $CH_3$ or H and Y is covalent bond or $—CO_2—$.

DETAILED DESCRIPTION OF INVENTION

Preferred are two, three and four monomer mixtures containing 30 to 70 weight % of the monomers of part A and 70 to 30 weight % of the monomers of part B. More preferred are two and three monomer mixtures containing 30 to 70 weight % of one monomer of part A and 70 to 30 weight % of one or two of the monomers of part B. Most preferred is a composition having equal amounts of three monomers, wherein n is 6, 8 and 10 and R is $CH_3$.

The synthesis of these monomers is known in the art. For instance, monomers where Y is covalent bond have been prepared by alkylation of 4'-(hydroxy)-4-cyanobiphenyl with omega-bromoalcohols followed by esterification of the alcohol with acryloyl or methacryloyl chloride. V. P. Shibaev, S. G. Kostromin and N. A. Plate, Eur. Polym. J., 18, 651 (1982).

Monomers where Y is $—CO_2—$ have been prepared by alkylation of 4-hydroxybenzoic acid with omega-chloroalcohols, esterification of the resulting alcohol with acrylic acid or methacrylic acid, conversion of the 4-substituted benzoic acid to an acid chloride and esterification of the acid chloride with 4-cyanophenol. M. Portugal, H. Ringsdorf, R. Zentel, Makromol. Chem., 183, 2311 (1982).

These polymerizable nematic mesophases are useful in the formation of polymeric films, particularly those having multi-oriented mesogens as described in U.S. patent application Ser. No. 490,115 (filed Mar. 7, 1990 now abandoned) and Ser. No. 605,724 (filed Oct. 29, 1990 now U.S. Pat. No. 5,073,294). Photopolymerization is initiated with UV irradiation.

A small amount of photoinitiator, preferably 0.5–2.0 wt %, is added to the polymerizable monomer composition to enhance the reactivity of the composition toward UV radiation. Examples of photoinitiators which will be useful to practice the present invention are benzophenone, 2,2-dimethoxy-2-phenylacetophenone, 2,2-diethoxyacetophenone, 2-benzoyloxyacetophenone, 2-chlorothioxanthone and 2-hydroxycyclohexyl phenyl ketone.

Multifunctional monomers, useful as crosslinking agents, can be added to the monomeric liquid crystals if desired. Conventional crosslinking agents are generally added at levels of about 0.5 to about 5 weight percent.

The compositions of this invention, when melted, exhibit nematic mesophases when cooled to near room temperature. One advantage of the compositions of this invention is their increased stability as compared to the nematic monomers by themselves and in other mixtures. The stability of the compositions of this invention offer significant advantage in processing. Once the monomer mixture is melted and cooled into the nematic phase, time is required to align the material on a substrate, to fill a cell, or to conduct other processing. In this period of time it is important that the nematic phase not undergo crystallization since crystallization of one or more of the monomers destroys the mesophase. The compositions of this invention have been found to be stable for periods of 12 or more hours.

The invention is described in the following examples, which are intended to be exemplary and not limiting, and wherein all parts, percentages, etc., are by weight unless otherwise noted.

EXAMPLE 1

This example illustrates the formation of intermediates used in the synthesis of monomers 1a, 1b, 1c, 1d, 1e, 1f and 1g.

1a—Formation of 4'-(6-bromohexyloxy)-4-cyanobiphenyl

A mixture of 4'-hydroxy-4-cyanobiphenyl (7.8 g, 40 mmol), potassium carbonate (8.3 g, 60 mmol), 1,6-dibromohexane (29.8 g, 120 mmol), and acetone (80 mL) was heated to reflux for 6 hours under a nitrogen atmosphere. The acetone was concentrated and the residue dissolved in ether-dichloromethane (4:1, 400 mL). The solution was filtered through glass fiber. The filtrate was washed with water and brine, dried over magnesium sulfate, and concentrated. Excess 1,6-dibromohexane was removed by Kugelrohr distillation up to 75° C. at 0.1 mm Hg. The material remaining in the pot was recrystallized from ethanol (100 mL), filtered while hot, and cooled in the freezer to give crystals of the bromide (9.6 g, 67%): mp 65.5°-66° C., mesophase at 63° C. in cooling; NMR (CDCl3) 7.55(s, 4H), 7.49(d, 2H), 6.82(d, 2H), 3.91(t, 2H), 2.0-1.3(m, 8H); IR (CH2Cl2) 2222, 1602 cm−1.

1b—Formation of 4'-(8-bromooctyloxy)-4-cyanobiphenyl

Treatment of 4'-hydroxy-4-cyanobiphenyl with 1,8-dibromooctane as described above gave crystals of the bromide (10.9 g, 69%): mp 79°-80° C.; NMR (CDCl3) 7.55(s, 4H), 7.50(d, 2H), 6.85(d, 2H), 3.9(t, 2H), 3.35(t, 2H), 1.9-1.3(m, 12H).

1c—Formation of 4'-(10-bromodecyloxy)-4-cyanobiphenyl

Treatment of 4'-hydroxy-4-cyanobiphenyl with 1,10-dibromodecane as described above gave crystals of the bromide (13.0 g, 78%): mp 69°-71° C.; NMR (CDCl3) 7.6(s, 4H), 7.5(d, 2H), 6.9(d, 2H), 3.95(t, 2H), 3.35(t, 2H), 1.95-1.3(m, 16H); IR (KBr) 2238, 2222, 1605 cm−1.

1d—Formation of 4'-(12-bromododecyloxy)-4-cyanobiphenyl

Treatment of 4'-hydroxy-4-cyanobiphenyl with 1,12-dibromododecane as described above gave crystals of the bromide.

1e—Formation of 4'-(5-bromophentyloxy)-4-cyanobiphenyl

Treatment of 4'-hydroxy-4-cyanobiphenyl with 1,5-dibromopentane as described above gave crystals of the bromide.

1f—Formation of 4'-(9-bromononyloxy)-4-cyanobiphenyl

Treatment of 4'-hydroxy-4-cyanobiphenyl with 1,9-dibromononane as described above gave crystals of the bromide.

1g—Formation of 4'-(11-bromoundecyloxy)-4-cyanobiphenyl

Treatment of 4'-hydroxy-4-cyanobiphenyl with 1,11-dibromoundecane as described above gave crystals of the bromide.

EXAMPLE 2

This example illustrates the formation of methacrylate monomers 1a, 1b, 1c, 1d, 1e, 1f and 1g.

Methacrylate Monomer 1a

A mixture of 4'-(6-bromohexyloxy)-4-cyanobiphenyl (7.0 g, 20 mmol), prepared as described in Example 1; potassium methacrylate (4.8 g, 40 mmol), hydroquinone (10 mg), and distilled dimethylformamide (40 mL) was heated to 70°-80° C. for 3 hours. The mixture was diluted with water (200 mL) and extracted with ether-dichloromethane (4:1, 200 mL portions, 2 times). The extract was washed with water, dried over magnesium sulfate, and concentrated. The resulting solid was recrystallized from absolute ethanol (90 mL), filtered and cooled in the freezer to obtain crystals of 1a (5.5 g, 76%): mp 74°-76° C.; NMR (CDCl3) 7.55(s, 4H), 7.45(d, 2H), 6.88(d, 2H), 6.0(s, 1H), 5.45(s, 1H), 1.95-1.3(m, 11H); IR (KBr) 2225, 1708 cm−1.

Methacrylate Monomer 1b

The bromide described in Example 1 was treated with potassium methacrylate as described above to give 1b as crystals (4.9 g, 63%): mp 71°-73° C.; NMR (CDCl3) 7.6(s, 4H), 7.48(d, 2H), 6.9(d, 2H), 6.03(s, 1H), 5.5(s, 1H), 4.02(m, 4H), 2.0-1.3(m, 12H).

Methacrylate Monomer 1c

The bromide described in Example 1 was treated with potassium methacrylate as described in above to give 1c as crystals (5.9 g, 66%): mp 69°-70° C., mesophase 47° C. in cooling cycle; NMR (CDCl3) 7.53(s, 4H), 7.4(d, 2H), 6.85(d, 2H), 5.95(s, 1H), 5.45(s, 1H), 4.0(m, 4H), 2.0-1.3(m, 19H).

Methacrylate Monomers 1d, 1e, 1f and 1g

The bromides prepared in Example 1 were treated with potassium methacrylate as described above to give 1d, 1e, 1f and 1g. Their melting points are listed in Table 1.

EXAMPLE 3

This example illustrates the formation of 4-(10-hydroxydecyloxy)benzoic acid and 4-(6-hydroxyhexyloxy)benzoic acid, intermediates in the preparation of monomers 2a and 2b.

4-(10-hydroxydecyloxy)benzoic

A mixture of 4-hydroxybenzoic acid (69.0 g, 0.5 mol), 10-chloro-1-decanol (106 g, 0.55 mol), potassium hydroxide (75 g, 1.15 mol), potassium iodide (0.1 g), and absolute ethanol (300 mL) was heated to reflux with mechanical stirring for 18 hours. The mixture was diluted with water (800 mL) and stirred 0.5 hours at room temperature. The mixture was acidified with 12N hydrochloric acid (125 mL) and the mixture stirred for 5 hours. The material was allowed to sit overnight and filtered. The solid was washed with water and air dried 4 days. The solid was recrystallized from tetrahydrofuran (300 mL) to give 4-(10-hydroxydecyloxy)benzoic acid (85.2 g, 58%): mp 115°-117° C.; NMR (CDCl3+d6 DMSO) 7.93(d, 2H), 6.85(d, 2H), 4.0(t, 2H), 3.52(t, 2H), 3.48(bs, 1H), 1.9-1.2(m, 16H).

4-(6-hydroxyhexyloxy)benzoic acid

A mixture of 4-hydroxybenzoic acid (138 g, 1.0 mol) and 6-chloro-1-hexanol (150 g, 1.1 mol) was treated as described above to give a solid (101.2 g, mp 127°-132° C.). Recrystallization of a portion of the solid from tetrahydrofuran gave pure 4-(6-hydroxyhexyloxy)benzoic acid: mp 132°-135° C.

EXAMPLE 4

This example illustrates the formation of 4-(10-methacryloxydecyloxy)benzoic acid and 4-(6-methacryloyloxyhexyloxy)benzoic acid, intermediates in the preparation of monomers 2a and 2b.

4-(10-methacryloxy-decyloxy)benzoic acid

A mixture of 4-(10-hydroxydecyloxy)benzoic acid (11.75 g, 40 mmol, prepared as described in Example 7), methacrylic acid (34.4 g, 0.4 mol), hexane (90 mL), toluene (130 mL), p-toluene sulfonic acid (1.0 g), and hydroquinone (0.2 g) was refluxed in a Dean-Stark apparatus for 4.5 hours. The mixture was cooled to room temperature and insoluble solids were filtered off. The filtrate was washed several times with water (1 L total), dried over magnesium sulfate and concentrated. The excess methacrylic acid was removed by Kugelrohr distillation up to 70° C. at 0.1 mm Hg. The remaining residue was dissolved in tetrahydrofuran (40 mL) and diluted with hexane (300 mL). A small amount of insoluble material was filtered off and the solution cooled to give a white solid (6.5 g, mp 62°-102° C.). Column chromatography (silica gel; hexane:ethyl acetate, 4:1) gave a purified sample (5.2 g, 36%): mp 61°-103° C., smectic mesophase in the cooling cycle, 103° C.; NMR (CDCl3) 9.45(bs, 1H), 8.03(d, 2H), 6.9(d, 2H), 6.03(s, 1H), 5.5(s, 1H), 4.1(t, 2H), 3.97(t, 2H), 1.9(s, 3H), 1.8-1.2(m, 16H).

4-(6-methacryloyloxyhexyloxy)benzoic acid

A solution of 4-(6-hydroxyhexyloxy)benzoic acid (24.0 g, 0.10 mol, prepared as described in Example 3) was treated with methacrylic acid as described above to give 4-(6-methacryloylhexyloxy)benzoic acid after recrystallization from tetrahydrofuran-hexane (1:2) (19.9 g, 67%): mp 81°-94° C., nematic mesophase; NMR (CDCl3) 9.82(bs, 1H), 8.0(d, 2H), 6.87(d, 2H), 6.05(s, 1H), 4.15(t, 2H), 4.0(t, 2H), 1.9(s, 3H), 1.85(m, 8H).

EXAMPLE 5

This example illustrates the formation of monomers 2a and 2b.

Monomer 2a

A solution of 4-(10-methacryloyloxydecyloxy)benzoic acid (3.62 g, 10 mmol) in toluene (30 mL) was stirred with oxalyl chloride (15 mmol, 1.91 g) and 1 drop of dimethylformamide for 3 hours at room temperature. Excess oxalyl chloride and toluene (10 mL) was distilled under reduced pressure. To the acid chloride solution was added 4-cyanophenol (1.43 g, 12 mmol), dichloromethane (10 mL) and triethylamine (21 mmol), consecutively. The mixture was heated to 60°-65° C. in an oil bath for 1 hours. The mixture was cooled, diluted with ether (150 mL) and washed with 1N hydrochloric acid, water, and brine. The ether solution was dried over magnesium sulfate, concentrated, and recrystallized from ethanol to give a solid (3.90 g). Further purification by column chromatography (silica, hexane-ether; 4:1) and recrystallization from ethanol gave monomer 2a (3.6 g, 78%): mp 59.5°-59.7° C., crystallized in the cooling cycle at 53° C.; NMR (CDCl3) 8.03(d, 2H), 7.62(d, 2H), 7.25(d, 2H), 6.88(d, 2H), 6.0(s, 1H), 5.45(s, 1H), 4.2-3.9(m, 4H), 1.9(s, 3H), 1.8-1.2(m, 16H); IR (KBr) 2225, 1730, 1720, 1712, 1640, 1603 cm−1.

Monomer 2b

A solution of 4-(6-methacryloyloxyhexyloxy)benzoic acid (8.9 g, 30 mmol, prepared as described in Example 4) was treated as described above to give a white solid (6.75 g, 55%, mp 54°-57° C.). Further purification by silica gel chromatography (hexane-ether, 3:1) and recrystallization from ethanol gave pure monomer 2b: mp 64.3°-65.3° C.; nematic phase in cooling cycle, 40.2° C.; NMR (CDCl3) 8.05(d, 2H), 7.67(d, 2H), 7.28(d, 2H), 6.90(d, 2H), 6.02(s, 1H), 5.5(s, 1H), 4.25-3.9(m, 4H), 1.9(s, 3), 1.85-1.30(m, 8H); IR (CHCl3) 2225, 1738, 1715, 1635, 1600 cm−1.

TABLE 1

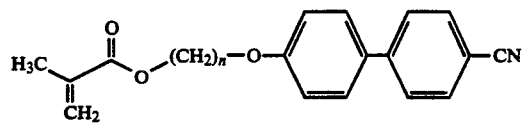

| Compound # | n | Melting Point (°C.) |
|---|---|---|
| 1a | 6 | 74–76 |
| 1b | 8 | 71–73 |
| 1c | 10 | 69–70 (47.0 nematic) |
| 1d | 12 | 66.0–67.5 |
| 1e | 5 | 67–68 |
| 1f | 9 | 74.5–75.5 |
| 1g | 11 | 73.3–74.0 |

Numbers in parenthesis refer to the cooling cycle.

TABLE 2

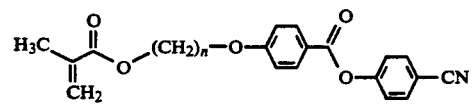

| Compound # | n | Melting Point (°C.) |
|---|---|---|
| 2a | 10 | 59.5–59.7 |
| 2b | 6 | 64.3–65.3 (40.2 nematic) |

EXAMPLE 6

This example illustrates the mixing of monomers to obtain formulations exhibiting monotropic nematic mesophases.

Monomers 1a (45 mg) and 1c (45 mg) were mixed and melted in a hot air stream to give a nematic fluid. A sample of this mixture was prepared between a microscope slide and a cover slip and heated above the isotropic point in a Mettler FP5 hotstage using a Mettler FP52 temperature control. The sample was cooled 3° C. per minute. A nematic phase was evident from 43.8° C. to room temperature. The nematic phase crystallizes over a period of about 1 day at room temperature.

EXAMPLE 7

This example further illustrates the mixing of monomers to obtain monotropic nematic mesophases.

Monomers 1a (90 mg), 1b (90 mg) and 1c (90 mg) were mixed and melted to give a nematic fluid. A sample of this material exhibited a nematic phase in the cooling cycle from 43.0° C. to room temperature. The sample crystallized in about 2 days at room temperature.

EXAMPLE 8

This example further illustrates the mixing of monomers to obtain monotropic nematic mesophases.

Monomers 2a (102 mg) and 2b (102 mg) were mixed and melted to give a nematic fluid that exhibited a nematic phase in the cooling cycle from 44.0° C. to room temperature. The material crystallized in about one day at room temperature.

EXAMPLE 9

This example illustrates the effect of added photoinitiator on the nematic mesophase temperature range.

2,2-Dimethoxy-2-phenylacetophenone (Irgacure 651, Ciba-Giegy, Ardsley, N.Y.) (5 mg, 2.5 wt %) was added to the mixture described in the previous example. The mixture was heated to make a homogeneous mixture. The mixture exhibited a nematic phase in the cooling cycle from 36.5° C. to room temperature. The material crystallized over a period of about 1 day at room temperature.

EXAMPLE 10

This example illustrates mixing of monomers using a homolog with an odd number of carbons in the alkylene tail.

Monomers 1a (50 mg), 1b (50 mg), and 1f (50 mg) were mixed and melted in a hot air stream to give a nematic fluid. A sample of this mixture was prepared between a microscope slide and a cover slip and heated above the isotropic point in a Mettler FP5 hotstage using a Mettler FP52 temperature control. The sample was cooled at 3° C. per minute. A nematic phase was evident from 44.5° C. to room temperature. The nematic phase crystallizes over a period of about 20 minutes at room temperature.

EXAMPLE 11

This example illustrates mixing of monomers using homologs with an odd number of carbons in the alkylene tail.

Monomers 1f (50 mg) and 1g (50 mg) were mixed and melted in a hot air stream to give a nematic fluid. The nematic fluid crystallized immediately at room temperature.

EXAMPLE 12

This example further illustrates mixing of monomers using homologs with an odd number of carbons in the alkylene tail.

Monomers 1e (50 mg), 1f (50 mg) and 1g (50 mg) were mixed and melted in a hot air stream to give a nematic fluid. A sample of this mixture was prepared between a microscope slide and a cover slip and heated above the isotropic point in a Mettler FP5 hotstage using a Mettler FP52 temperature control. The sample was cooled at 3° C. per minute. A nematic phase was evident from 47° C. to room temperature. The nematic phase crystallized within 10 minutes at room temperature.

These above examples demonstrate that compositions wherein n is an even number per the instant invention have significantly greater stability than the comparative samples wherein n is odd number of carbon atoms, which rapidly crystallize from the nematic phase.

EXAMPLE 13

This example illustrates the polymerization of a nematic monomer mesophase in a homeotropic orientation to give a polymer phase exhibiting the same orientation.

Glass microscope slides were cleaned by sonicating 0.5 hour in a 50:50 mixture of RBS-35 nonionic surfactant (Pierce Chemical Co., Rockford, Il, 61105) and deionized distilled water, followed by sequential sonication for 0.5 hour (each) with acetone, methanol, and deionized distilled water.

To the nematic monomer mixture described in Example 7 was added 1 weight % of Irgacure 651. Then, the nematic monomer composition was placed on a cleaned glass microscope slide at 50°–60° C. while shielding it from light. The sample was sandwiched with a second clean slide by using 10 micron glass fiber spacers. The sample was cooled to room temperature and allowed to sit to develop uniform homeotropic orientation. The sample was then exposed to UV light (200 watt Hg arc, 6–9 inches from the source) for 1 minute. A frozen homeotropic orientation was obtained. The plates were removed to give a free standing film.

While this invention has been described with respect to specific embodiments, it should be understood that these embodiments are not intended to be limiting and that many variations and modifications are possible without departing from the cope of this invention.

What is claimed is:

1. A polymerizable nematic monomer composition consisting essentially of (A) 20 to 80 weight % of at least one monomer having the general formula (I) wherein n is 10, 12 or 14, and (B) 80 to 20 weight % of at least one monomer having the general formula (I) wherein n is 4, 6 or 8:

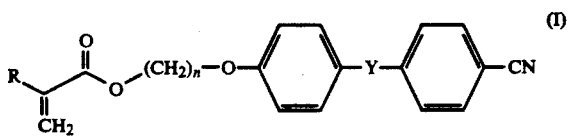

wherein R is $CH_3$ or H and Y is covalent bond or $-CO_2-$.

2. A polymerizable nematic monomer composition as claimed in claim 1 having a total of two, three or four monomers of the general formula (I), wherein (A) 30 to 70 weight % of the monomers of the general formula (I) have n is 10, 12 or 14 and (B) 30 to 70 weight % of the monomers of the general formula (I) have n is 4, 6 or 8.

3. A polymerizable nematic monomer composition as claimed in claim 1, containing (A) 30 to 70 weight % of one monomer having n is 10, 12 or 14 and (B) 30 to 70 weight % of one or two of the monomers having n is 4, 6 or 8.

4. A polymerizable nematic monomer composition as claimed in claim 1, further comprising 0.5 to 2.0 weight % photoinitiator.

5. A polymerizable nematic monomer composition as claimed in claim 4, wherein the photoinitiator is selected from the group consisting of benzophenone, 2,2-dimethoxy-2-phenylacetophenone, 2,2-diethoxyacetophenone, 2-benzoyloxyacetophenone, 2-chlorothioxanthone and 2-hydroxycyclohexyl phenyl ketone.

6. A polymerizable nematic monomer composition as claimed in claim 2, further comprising 0.5 to 2.0 weight % photoinitiator.

7. A polymerizable nematic monomer composition as claimed in claim 6, wherein the photoinitiator is selected from the group consisting of benzophenone, 2,2-dimethoxy-2-phenylacetophenone, 2,2-diethoxyacetophenone, 2-benzoyloxyacetophenone, 2-chlorothioxanthone and 2-hydroxycyclohexyl phenyl ketone.

8. A polymerizable nematic monomer composition as claimed in claim 3, further comprising 0.5 to 2.0 weight % photoinitiator.

9. A polymerizable nematic monomer composition as claimed in claim 8, wherein the photoinitiator is selected from the group consisting of benzophenone, 2,2-dimethoxy-2-phenylacetophenone, 2,2-diethoxyacetophenone, 2-benzoyloxyacetophenone, 2-chlorothioxanthone and 2-hydroxycyclohexyl phenyl ketone.

* * * * *